United States Patent
Guala

(10) Patent No.: US 10,373,307 B2
(45) Date of Patent: Aug. 6, 2019

(54) METHOD AND DEVICE FOR CHECKING A JOINT BETWEEN TWO COMPONENTS OF A MEDICAL DEVICE

(71) Applicant: Industrie Borla S.p.A., Moncalieri (Turin) (IT)

(72) Inventor: Gianni Guala, Turin (IT)

(73) Assignee: INDUSTRIE BORLA S.P.A., Moncalieri, Turin (IT)

(*) Notice: Subject to any disclaimer, the term of this patent is extended or adjusted under 35 U.S.C. 154(b) by 58 days.

(21) Appl. No.: 15/556,905

(22) PCT Filed: Mar. 11, 2016

(86) PCT No.: PCT/IB2016/051402
§ 371 (c)(1),
(2) Date: Sep. 8, 2017

(87) PCT Pub. No.: WO2016/142920
PCT Pub. Date: Sep. 15, 2016

(65) Prior Publication Data
US 2018/0033135 A1 Feb. 1, 2018

(30) Foreign Application Priority Data
Mar. 11, 2015 (IT) .................. 102015000008211

(51) Int. Cl.
*G06T 7/00* (2017.01)
*A61M 5/14* (2006.01)
(Continued)

(52) U.S. Cl.
CPC .......... *G06T 7/0004* (2013.01); *A61M 5/1411* (2013.01); *A61M 5/162* (2013.01);
(Continued)

(58) Field of Classification Search
CPC .. A61M 5/1411; A61M 5/162; A61M 5/3213; A61M 5/34; A61M 2207/00;
(Continued)

(56) References Cited

U.S. PATENT DOCUMENTS 5,375,722 A * 12/1994 Leary ............... B31B 50/00
 209/3.3
6,069,693 A * 5/2000 Licchesi ............... G01N 21/88
 356/237.1

(Continued)

FOREIGN PATENT DOCUMENTS

CN 203425993 U 2/2014
EP 0736304 A1 * 10/1996 .......... A61M 5/1411
(Continued)

OTHER PUBLICATIONS

Patent Cooperation Treaty, Notification of Transmittal of the International Search Report and the Written Opinion of the International Searching Authority, or the Declaration for PCT/IB2016/051402 dated Jul. 14, 2016, 12 pages.

*Primary Examiner* — Zhihan Zhou
(74) *Attorney, Agent, or Firm* — Heslin Rothenberg Farley & Mesiti P.C.; Victor A. Cardona, Esq.

(57) ABSTRACT

A method for checking a faultless joint between a first and a second component of a medical device, namely a drip chamber and a spike, wherein the first component has an annular coupling edge facing downwardly to be sprayed interiorly with a liquid solvent. The solvent is mixed with a tracer detectable through ultraviolet or infrared light and the coupling edge is illuminated with a ultraviolet or infrared light so as to make an image of the sprayed solvent, which is reflected and captured by an electronic scanning device configured to establish whether such image is faultless, visible through a tracer.

7 Claims, 4 Drawing Sheets

(51) Int. Cl.
*A61M 5/162* (2006.01)
*A61M 5/32* (2006.01)
*A61M 5/34* (2006.01)
*G01N 21/91* (2006.01)

(52) U.S. Cl.
CPC ............ *A61M 5/3213* (2013.01); *A61M 5/34* (2013.01); *G01N 21/91* (2013.01); *A61M 2205/3313* (2013.01); *A61M 2205/70* (2013.01); *A61M 2207/00* (2013.01); *G06T 2207/10048* (2013.01); *G06T 2207/30204* (2013.01)

(58) Field of Classification Search
CPC ...... A61M 2205/3313; A61M 2205/70; G06T 2207/30204; G06T 7/0004; G06T 2207/10048; G01N 21/91
See application file for complete search history.

(56) References Cited

U.S. PATENT DOCUMENTS

| | | | |
|---|---|---|---|
| 2010/0063456 A1* | 3/2010 | Rahimy | A61J 1/1475 604/244 |
| 2010/0304008 A1 | 12/2010 | Lauria et al. | |
| 2013/0023966 A1* | 1/2013 | Depfenhart | A61B 18/203 607/89 |
| 2013/0064967 A1* | 3/2013 | Feinstein | B05C 9/12 427/8 |
| 2014/0097350 A1* | 4/2014 | Reichelsheimer | B32B 37/1284 250/372 |

FOREIGN PATENT DOCUMENTS

| | | |
|---|---|---|
| EP | 0736304 A1 | 10/1996 |
| EP | 1146330 A2 | 10/2001 |

* cited by examiner

METHOD AND DEVICE FOR CHECKING A JOINT BETWEEN TWO COMPONENTS OF A MEDICAL DEVICE

CROSS REFERENCE TO RELATED APPLICATIONS

This application is a national stage filing under section 371 of International Application No. PCT/IB2016/051402, filed on Mar. 11, 2016, published in English on Sep. 15, 2016, as WO2016/142920 A1 and which claims priority to Italian Application No. 102015000008211, filed on Mar. 11, 2015, the entire disclosure of these applications being hereby incorporated herein by reference.

FIELD OF THE INVENTION

The present invention generally refers to medical devices of the type in which a first component made of plastic material is joined to a second component also made of plastic material by bonding, typically using a liquid glue or solvent.

STATE OF THE PRIOR ART

A medical device of this type, for example as described in EP-0736304A1, consists in a drip chamber for the infusion of a liquid medicine from a bag to a line connected to a patient, and a spike axially fixed to the drip chamber. In this case, the drip chamber and the spike respectively constitute the first and the second component and they are joined to each other according to common vertical axis at respective mutual coupling annular edges. When manufacturing a medical device thus made, the drip chamber is positioned with the relative annular coupling edge facing downwards so as to be sprayed interiorly, from beneath upwards, with a dose of the liquid glue or solvent. Such annular edge is then axially engaged with the corresponding annular edge of the spike, facing upwards, and the two components are then joined together to form the medical device.

Though this assembly method implemented by the Applicant is entirely mechanised, with extremely high production rate, currently it does not offer the possibility of efficiently checking the joint between the two components unless through a sample check by an operator.

The liquid glue or solvent with which the annular coupling edge of the first component is sprayed, is dosed from above downwards and the only automatic check currently carried out consists in detecting the dispensing. However, even in cases where the jet is detected, it may not be sufficient or enough to avoid faulty joint between the two components. Possible defects may lead to inadvertent separation between the two components and this, in medical applications where the device is used, may even lead to serious and unacceptable risks.

Optical systems for checking the joint between two components are known in other sectors of the industry.

For example, U.S. Pat. No. 5,375,722A describes a monitoring system for checking the glue applied along the edges of carton panels, which provides for mixing the glue with a fluorescent tracer, illuminating the applied glue with UV light and detecting the reflected light by means of a sensor. The sensor is simply capable of checking for the presence or absence of the glue but it does not establish whether the gluing between the two components is correct or faulty.

Even patent no EP-1146330 provides for checking the application of an adhesive on a wooden panel through the illumination of UV light, which is absorbed by the adhesive at a lower amount than the wood, detecting the images of the area with greater or lesser light intensity by means of a video camera and assessing them through an image processing system. However, in his case the UV light emitter and the video camera are positioned on opposite sides with respect to the piece subject of analysis. this arrangement is entirely unsuitable for use in a medical devices production line, in which the gluing station between the two components of the device is typically constituted by a rotary turntable. Thus, it is technically necessary that the UV or infrared light emitter and the receiver of the image reflected from the gluing area between the two components be arranged outside the turntable, thus on the same side.

SUMMARY OF THE INVENTION

Thus, the object of the invention is to overcome the aforementioned technical problem in an efficient and safe manner, and this object is attained thanks to a method as defined in the pre-characterising part of claim 1, characterised in that:
 the glue or solvent is mixed with a tracer detectable by ultraviolet or infrared light,
 the coupling edge of the first component, after being sprayed with the glue or solvent, is illuminated with ultraviolet or infrared light along a first direction forming a first angle with the vertical axis, so as to make an image of the sprayed glue or solvent visible by means of the tracer,
 the image is reflected along a second direction forming a second angle with the aforementioned vertical axis and it is captured by an electronic scanning device configured to establish whether the image is faultless so that, in the negative case, said medical device is discarded, and
 the ultraviolet or infrared illuminates said coupling edge of the first component through a semitransparent mirror through which said image of the sprayed glue or solvent made visible by said tracer is reflected towards the electronic scanning device.

Any defect detected by the electronic scanning device, typically constituted by a video camera, may lie in the fact that the glue or solvent is not present, or is only partly present without the geometric precision required to consider a medical device acceptable or inacceptable, bearing in mind the criticalities related to the use of such device, or there is an excessive amount of it. Thus, the electronic analysis of the captured image allows establishing such situations and thus evaluating whether, after mutually coupling the two components thereof, the medical device is suitable or unsuitable for the purpose.

The checking method implemented according to the invention may be advantageously implemented along the mechanised assembly line, with limited overall dimension spaces and without altering the production rate in any manner whatsoever, by means of a simple and economic device also part of the present invention.

BRIEF DESCRIPTION OF THE DRAWINGS

The invention will now be described in detail, purely by way of non-limiting example, with reference to the attached drawings, wherein.

DETAILED DESCRIPTION OF THE INVENTION

Figure 1:
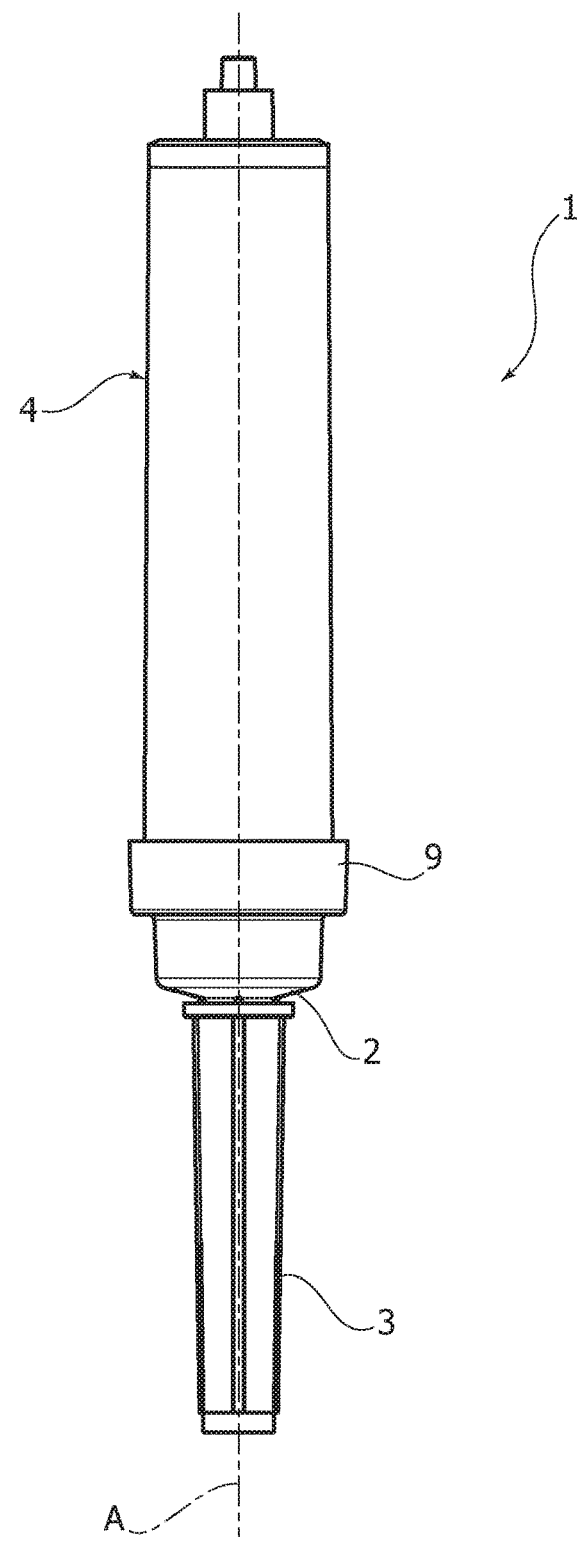
FIG. 1 is an elevational schematic view of an example of medical device to which the method according to the invention may advantageously apply.
Figure 2:
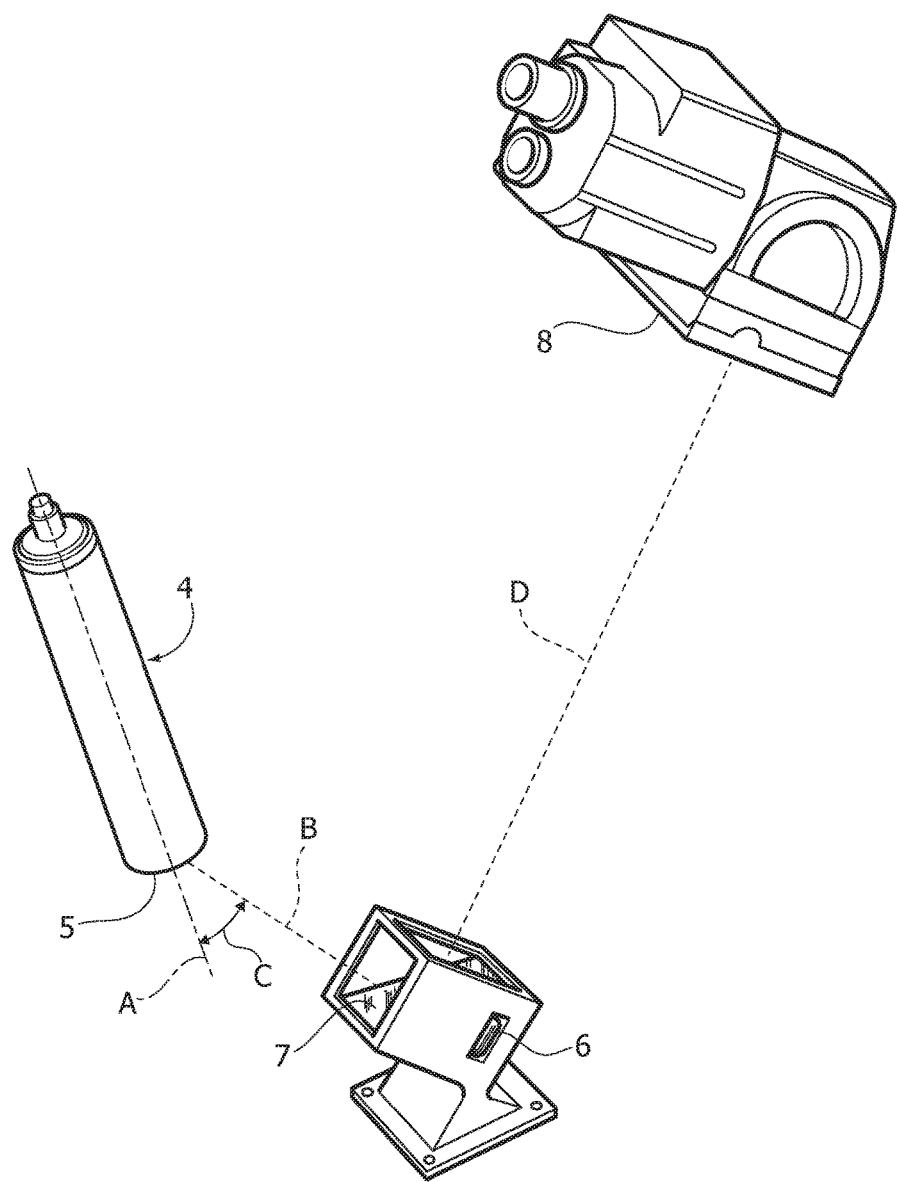
FIG. 2 is a schematic perspective view that exemplifies the mode of implementation of the method according to the invention.
Figure 3:
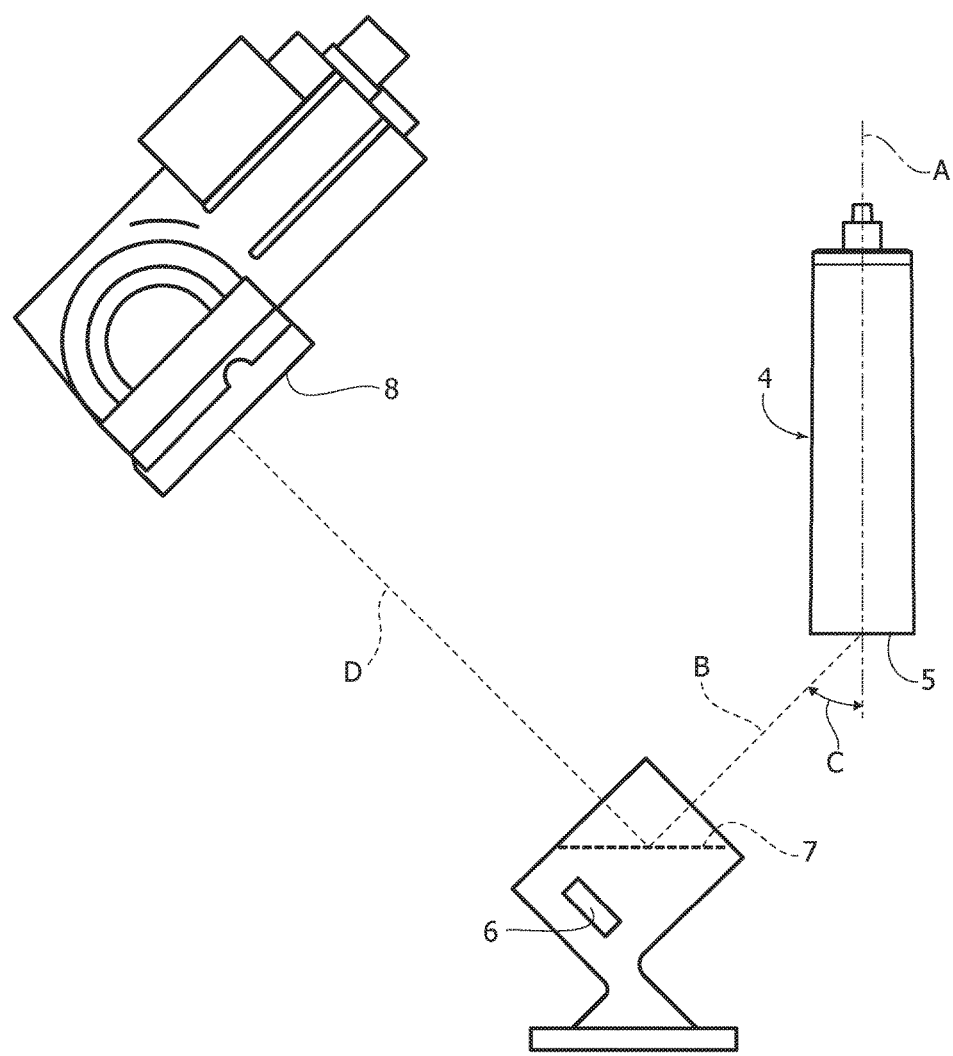
FIG. 3 is a side elevational view and rotated by 180° of FIG. 2.
Figure 4:
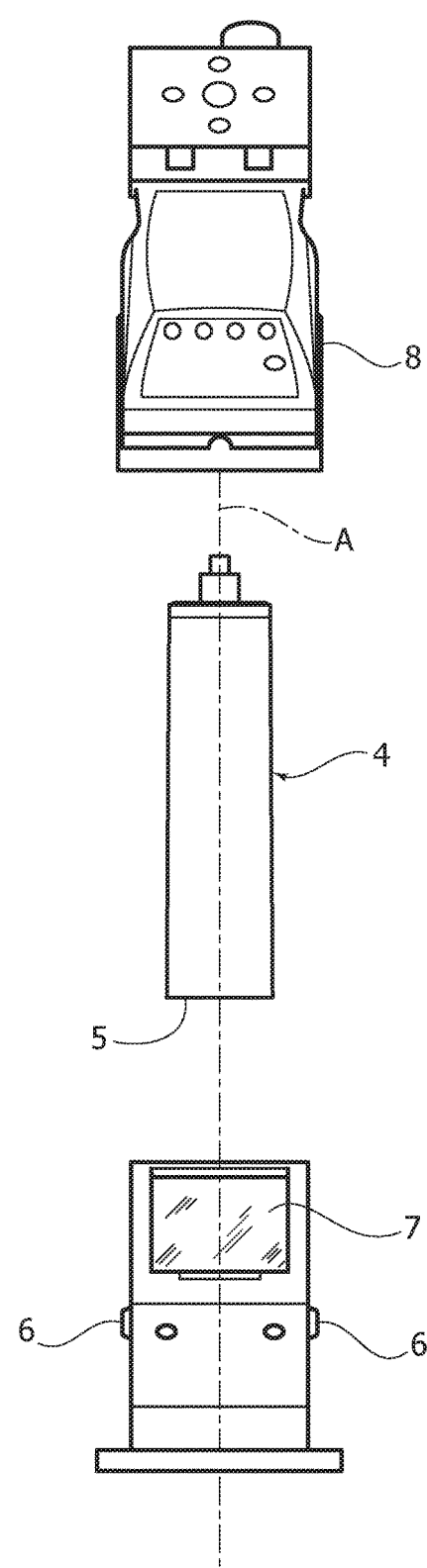
FIG. 4 is a front view of FIG. 2.

Initially with reference to FIG. 1, a medical device to which the method according to the invention may advantageously apply consists in a tubular body 1 formed by a spike 2 (protected by a removable protection cap 3 in the illustrated example) and a drip chamber 4. The device 1 is represented at the end of the manufacturing thereof, with the drip chamber 4 having an annular coupling edge 5 (FIGS. 2-4) facing downwards and engaged with a complementary annular coupling edge 9, facing upwards, of the spike 2. Obviously, during use the spike 2 shall be positioned above and the drip chamber 4 shall be positioned beneath.

The spike 2 and the drip chamber 4, both made of plastic material and the second preferably transparent, are joined to each other according to a common vertical axis A through the adhesion between the respective annular coupling edges 5 and 9 obtained using a glue, conveniently constituted by a liquid solvent.

The method of assembly between the components 2 and 4 consists, in an entirely conventional manner, in spraying the annular coupling edge 5 of the drip chamber 4 with a dose of liquid solvent capable of allowing wetting the inner surface of the coupling edge, and thus axially engaging such coupling edge 5 with the coupling edge 9 of the spike 2.

The method according to the invention is implemented before the coupling operation, and it provides for the following steps.

Firstly, the solvent used for joining is mixed with a tracer, for example a powder fluorescent reagent detectable through ultraviolet light (or, according to a variant, with tracer detectable by infrared radiation).

Then, the inner surface of the coupling edge 5 of the drip chamber 4, positioned with the axis A thereof arranged vertically, is sprayed with the solvent, by means of a spray from beneath upwards as explained previously.

Such surface is then illuminated with ultraviolet light by means of a UV source 6. The ultraviolet light is sent towards the coupling edge 5, by means of an inclined semitransparent mirror 7, along a direction B that is not parallel to the vertical axis A, but forms an angle C, for example 45°, therewith. For this purpose, the UV source 6 is positioned at a lower level with respect to the drip chamber 4, and it is laterally offset with respect to the latter.

Thus, the ultraviolet light makes an image of the inner surface of the annular edge 5, sprayed with the solvent, visible by means of the tracer contained in the solvent. Such image is reflected on the reflecting surface of the semitransparent mirror 7 and diverted along a second direction D, orthogonal to the first direction B in this case, towards an electronic scanning device typically constituted by a video camera 8. The image captured by the video camera 8 is then electronically checked to establish whether it is correct or faulty due to the fact that the solvent is not present or is only partly present. In the second case the drip chamber 4, or the device 1 formed by such drip chamber 4 to which the spike 2 was subsequently applied, is discarded automatically.

The method according to the invention is advantageously applicable in production lines of the rotary turntable type, and the device for the implementation thereof, formed by the light source 6, the semitransparent mirror 7 and the video camera 8, is extremely simple and small in size, and it does not interfere with the production rate in any manner whatsoever.

Obviously, the modes of implementation of the method may widely vary with respect to what has been described and illustrated, without departing from the scope of protection of the present invention as described in the claims that follow. Thus, as mentioned, the tracer mixed with the liquid solvent may be of the type detectable by infrared radiation, and in this case the video camera may be a thermal imaging camera.

The invention claimed is:

1. A method for checking a faultless joint between a first and a second component of a medical device, the method comprising:

connecting said first and second components to each other along a common vertical axis utilizing a rotary turntable by arranging the first component with a respective annular coupling edge facing downwardly and spraying the edge interiorly, from beneath upwards, with a liquid glue or solvent and then axially engaging the edge with a corresponding annular coupling edge facing upwardly of the second component, thereby making said first and second components mutually fixed so as to form said medical device, said glue or solvent mixed with a tracer detectable by ultraviolet or infrared light, passing ultraviolet or infrared light through a semi-transparent mirror and illuminating said coupling edge of the first component with the ultraviolet or infrared light after the spraying the edge with the glue or solvent, the illuminating with the ultraviolet or infrared light being along a first direction forming a first angle with said vertical axis, so as to make an image of the sprayed glue or solvent visible by means of said tracer, reflecting said image by said semi-transparent mirror along a second direction and capturing said image by an electronic scanning device configured to determine whether said image is without defects, and discarding said medical device if said image has defects, and.

2. Method according to claim 1, wherein the electronic scanning device is a video camera.

3. The method of claim 1, wherein the first component comprises a drip chamber.

4. The method of claim 1, wherein the second component comprises a spike.

5. A device for checking a faultless joint between a first and a second component of a medical device, said device comprising:

a gluing station comprising a rotary turntable, said gluing station configured to spray glue or solvent on an edge of respective annular coupling edges of first and second components according a to common vertical axis to connect the edges to each other, the glue or solvent mixed with a tracer detectable by means of ultraviolet or infrared light;

a light source adapted to direct ultraviolet or infrared light through a semi-transparent mirror to illuminate said coupling edges, after being sprayed with the glue or solvent, the directing of the ultraviolet or infrared light along a first direction forming a first angle with said vertical axis, so as to make an image of the sprayed glue or solvent visible by means of said tracer, a video camera for capturing said image, and said semitransparent mirror reflecting said image along a second direction toward said video camera, said light source, said semi-transparent mirror, and said video camera located outside said rotary turntable.

6. The device of claim 5, wherein the first component comprises a drip chamber.

7. The device of claim 5, wherein the second component comprises a spike.

* * * * *

UNITED STATES PATENT AND TRADEMARK OFFICE
CERTIFICATE OF CORRECTION

PATENT NO.         : 10,373,307 B2                                           Page 1 of 1
APPLICATION NO.    : 15/556905
DATED              : August 6, 2019
INVENTOR(S)        : Gianni Guala It is certified that error appears in the above-identified patent and that said Letters Patent is hereby corrected as shown below:

In the Claims

Column 4, Line 43: Claim 1, Delete "defects, and." and insert -- defects. --

Signed and Sealed this
Twenty-fourth Day of September, 2019

Andrei Iancu
*Director of the United States Patent and Trademark Office*